United States Patent [19]

Clemence et al.

[11] 4,045,567
[45] Aug. 30, 1977

[54] 2-ALKYL-5-THIAZOLE-CARBOXYLIC ACID DERIVATIVES IN HYPOLIPEMIANT COMPOSITIONS

[75] Inventors: François Clémence, Rosny-sous-Bois; Odile Le Martret, Paris, both of France

[73] Assignee: Roussel Uclaf, France

[21] Appl. No.: 662,122

[22] Filed: Feb. 27, 1976

Related U.S. Application Data

[60] Continuation of Ser. No. 557,289, March 11, 1975, abandoned, which is a division of Ser. No. 431,881, Jan. 9, 1974, Pat. No. 3,882,110, which is a continuation of Ser. No. 244,909, April 17, 1972, abandoned, which is a continuation-in-part of Ser. No. 842,017, July 15, 1969, abandoned.

[30] Foreign Application Priority Data

June 11, 1969 France ............................... 69.19339

[51] Int. Cl.² .......................................... A61K 31/425
[52] U.S. Cl. .................................... 424/270; 260/253; 260/256; 260/293; 260/68; 260/294.8 D; 260/302 R; 260/302 H; 424/248.51; 424/253; 424/263; 424/267; 544/109
[58] Field of Search ................... 424/270, 248.51, 267, 424/253, 263

[56] References Cited

U.S. PATENT DOCUMENTS 3,476,766  11/1969  Brown ........................... 260/302 R

OTHER PUBLICATIONS

Geiger et al., Chem. Abstracts, 67:11413w, (1967).

*Primary Examiner*—Frederick E. Waddell
*Assistant Examiner*—Vera C. Clarke
*Attorney, Agent, or Firm*—Hammond & Littell

[57] ABSTRACT

Hypolipemiant compositions comprising an effective amount of at least one 2-alkyl-5-thiazole-carboxylic acid derivative of the formula

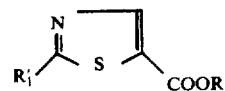

wherein R is hydrogen, an alkali metal, ammonium, the monovalent residue of an organic base or a substituted or unsubstituted alkyl and where $R'_1$ is a linear alkyl of 1 to 12 carbon atoms, and a major amount of a pharmaceutical carrier; as well as the method of reducing the amount of sanguine lipids in warm-blooded animals utilizing the above-hypolipemiant compositions.

12 Claims, No Drawings

2-ALKYL-5-THIAZOLECARBOXYLIC ACID DERIVATIVES IN HYPOLIPEMIANT COMPOSITIONS

REFERENCE TO A PRIOR APPLICATION

This application is a continuation of our U.S. patent application Ser. No. 557,289, filed Mar. 11, 1975 now abandoned, which in turn was a division of our copending U.S. patent application Ser. No. 431,881, filed Jan. 9, 1974, now U.S. Pat. No. 3,882,110, which in turn was a continuation of our copending U.S. patent application Ser. No. 244,909, filed Apr. 17, 1972, now abandoned, which in turn was a continuation-in-part of our copending U.S. patent application Ser. No. 842,017, filed July 15, 1969 now abandoned.

OBJECTS OF THE INVENTION

It is an object of the invention to provide novel 2-alkyl-5-thiazolecarboxylic acid derivatives of formula I.

It is another object of the invention to provide a novel process for the preparation of the compounds of formula I.

It is a further object of the invention to provide novel hypolipemiant compositions containing at least one 2-alkyl-5-thiazolecarboxylic acid compound of formula II.

It is an additional object of the invention to provide a novel method of reducing the amount of sanguine lipids in warm-blooded animals.

These and other objects and advantages of the invention will become obvious from the following detailed description.

DESCRIPTION OF THE INVENTION

The novel compounds of the invention are 2-alkyl-5-thiazolecarboxylic acid derivatives of the formula

I wherein R is hydrogen, an alkali metal, ammonium, the monovalent residue of an organic amine base or a substituted or unsubstituted alkyl, and R' is a linear alkyl of 3 to 12 carbon atoms.

The substituent R is preferably hydrogen, an alkali metal atom, such as sodium; ammonium; the salt of an organic amine base, for example, lower alkylammonium, such as methylammonium, di-lower alkylammonium, such as diethylammonium, diisopropylammonium, tri-lower alkylammonium, such as triethylammonium, lower alkylolammonium, such as ethanolammonium, di-lower alkylolammonium, such as diisopropanolammonium, collidinium, morpholinium, piperidinium; alkyl having 1 to 10 carbon atoms, such as methyl, ethyl, decyl; the alkyl residue of an aryl aliphatic alcohol, the aliphatic residue of which contains 1 to 6 carbon atoms, for example, phenylalkyl having 1 to 6 carbon atoms in the alkyl, where the phenyl can have substituents, such as alkyl having 1 to 6 carbon atoms, halogen and alkoxy having 1 to 6 carbon atoms, such as phenylmethyl, phenylethyl, p-chlorophenylethyl, p-methylphenylethyl, p-methoxyphenylethyl, phenoxyalkyl having 1 to 6 carbon atoms in the alkyl, where the phenoxy can have substituents such as alkyl having 1 to 6 carbon atoms, halogen and alkoxy having 1 to 6 carbon atoms, such as phenoxyethyl, 2-(p-chlorophenoxy)-2,2-dimethylethyl, p-methoxyphenoxyethyl; dialkylaminoalkyl having 4 to 10 carbon atoms, such as diethylaminoethyl, diethylaminopropyl, dipropylaminoethyl; alkylpolyol having 3 to 10 carbon atoms such as α-glyceryl or β-glyceryl; the alkyl residue of an alkylheterocyclic alcohol, the aliphatic residue of which contains 1 to 6 carbon atoms, for example, furylalkyl having 1 to 6 carbon atoms in the alkyl, such as α-furylethyl, thienylalkyl having 1 to 6 carbom atoms in the alkyl, such as 3-thienylpropyl, pyridylalkyl having 1 to 6 carbon atoms in the alkyl, such as N-pyridylethyl, β-pyridylethyl, theophyllinylalkyl having 1 to 6 carbon atoms in the alkyl, such as the ester of 7-hydroxymethyltheophylline, morpholinylalkyl having 1 to 6 carbon atoms in the alkyl, such as β-morpholinylethyl; and the ketonides of alkylpolyols having 3 to 10 carbon atoms, such as the acetonide of α-glyceryl.

Preferably, when R represents an ester of an alkanol or a substituted alkanol, the same has the partial formulae

wherein $n$ is an integer from 0 to 9, $m$ is an integer from 1 to 6 and $R_2$ is a member selected from the group consisting of alkylpolyol having 2 to 4 carbon atoms, di-lower alkylamino, a heterocyclic ring having 5 or 6 ring atoms and at least one hetero atom selected from the group consisting of nitrogen, sulfur and oxygen and from 3 to 5 carbon atoms, theophyllinyl, phenyl, halophenyl, lower alkylphenyl and lower alkoxyphenyl, as well as the acid addition salts of those compounds containing amino nitrogen atoms in the substituted alkanol.

The novel hypolipemiant composition of the invention contain at least one 2-alkyl-5-thiazolecarboxylic acid derivative of the formula II:

II wherein R has the above-assigned meaning and $R'_1$ is a linear alkyl of 1 to 12 carbon atoms.

The compounds of formula II are endowed with remarkable pharmacological properties. They manifest to varying degrees hypolipemiant activity as well as a very important an prolonged vasodilating action and a very definite anti-inflammatory action.

Preferred compounds of formula II are: 2-methyl-5-thiazolecarboxylic acid, already described by Schoberl and Stock (Berichte 73B [1940]1240)

2-ethyl-5-thiazolecarboxylic acid
2-propyl-5-thiazolecarboxylic acid
2-n-butyl-5-thiazolecarboxylic acid
2-n-pentyl-5-thiazolecarboxylic acid
2-n-hexyl-5-thiazolecarboxylic acid
2-n-undecyl-5-thiazolecarboxylic acid, as well as salts of the said acids and their esters, such as
diisopropylammonium 2-propyl-5-thiazolecarboxylate
ethyl 2-propyl-5-thiazolecarboxylate
N,N-diethylaminoethyl 2-propyl-5-thiazolecarboxylate and its chlorohydrate
2,3-isopropylidenedioxy-propyl 2-propyl-5-thiazolecarboxylate
phenylethyl 2-propyl-5-thiazolecarboxylate α-glyceryl 2-propyl-5-thiazolecarboxylate
methyl 2-propyl-5-thiazolecarboxylate
morpholinylethyl 2-propyl-5-thiazolecarboxylate and its chlorohydrate
tert. butyl 2-propyl-5-thiazolecarboxylate
benzyl 2-propyl-5-thiazolecarboxylate
pyridylmethyl 2-propyl-5-thiazolecarboxylate.

One can likewise mention the α-glycerol or β-gylcerol esters of 2methyl-, 2-ethyl- or 2-n-propyl-5-thiazolecarboxylic acids, the diethylaminoethyl or diethylaminopropyl or dipropylaminoethyl esters of the same acids.

One can likewise mention as good representatives of this family the esters of β-pyridylmethanol or of p-chlorophenoxy-isobutanol or of 7-hydroxymethyl-theophylline with the same acids.

The novel process of the invention for the preparation of compounds of formula I comprises reacting an alkylthioamide, of formula:

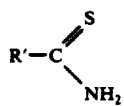

wherein R' is a linear alkyl of 3 to 12 carbon atoms with a lower alkyl 2-halogeno-3-oxo-propionate of formula

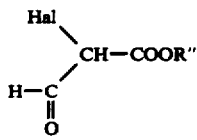

wherein Hal is a halogen atom other than fluorine and R" is a lower alkyl radical, such as ethyl, saponifying or hydrolyzing the resultant lower alkyl ester of 2-alkyl-5-thiazolecarboxylic acid to form a corresponding 2-alkyl-5-thiazolecarboxylic acid which may be, if desired, salified by the action of an alkaline or organic base, or esterified by the action of a substituted or unsubstituted alkanol of the formula ROH where R has the above-assigned values.

Preferably the alkyl 2-halogeno-3-oxo-propionate is ethyl 2-chloro-3-oxo-propionate; the condensation between the alkyl-thioamide and the alkyl 2-halogeno-3-oxo-propionate is effected in an organic solvent, such as an aromatic or cyclic hydrocarbon or an alkanol; the condensation between the alkyl thioamide and the alkyl 2-halogeno-3-oxo-propionate is effected at reflux of the solvent; the saponification of the alkyl ester of 2-alkyl-5-thiazolecarboxylic acid is effected by an alkaline agent such as an alkali metal hydroxide in a lower alkanolic solvent; the salification of the 2-alkyl-5-thiazolecarboxylic acid is effected by the action of an alkali metal base, in an aqueous medium; the salification of the 2-alkyl-5-thiazolecarboxylic acid by the action of an organic base is effected in an anhydrous or aqueous organic solvent, such as acetone or ethanol; the esterification of the 2-alkyl-5-thiazolecarboxylic acid is effected by the action of an alkanol, in the presence of an acid catalyst or by a diazoalkane.

The novel hypolipemiant compositions of the invention are comprised of at least one compound of formula II and a major amount of a pharmaceutical carrier. The compositions may be in the form of injectable solutions or suspensions, tablets, coated tablets, cachets, capsules, granules, emulsions, syrups and suppositories prepared in the usual manner.

The novel compositions of the invention may include one or more compounds of similar activity or synergistic effect, such as peripheral vasodilators, regulators of capillary permeability or antispasmodics.

The individual dose is 0.1 gm to 0.5 gm or from 1 mg/kg to 10 mg/kg, depending upon the method of administration.

The hypolipemiant compositions of the invention are useful for the treatment of acute or chronic hyperlipidemia, of atheromatosis, of hepatic or toxic steatosis, of lipid nephrosis and of circulatory trouble such as arteritis or vascular spasms.

The novel method of the invention of reducing the amount of sanguine lipids in warm-blooded animals comprises administering to warm-blooded animals a safe and effective amount of at least one compound of formula II.

The said compounds may be administered orally, rectally or transcutaneously.

The usual useful daily dose is from 8 to 45 mg/kg depending upon the method of administration.

In the following examples, there are described several preferred embodiments to illustrate the invention. However, it should be understood that the invention is not intended to be limited to the specific embodiments.

EXAMPLE I

2-Ethyl 5-thiazolecarboxylic acid ($R'_1 = CH_2CH_3$ an R = H)

A solution of 26 gm of thiopropionamide in 100 cc of ethanol is mixed with a solution of 36.5 gm of ethyl 2-chloro-3-oxo-propionate in 50 cc of ethanol. The reaction mixture is left in contact overnight, then the alcohol is evaporated off. The residue is dissolved in ether, the ethereal phase is washed with an aqueous 20% sodium carbonate solution, then with water. The oil obtained is distilled and the fraction coming off at 80° C to 90° C under a pressure of 0.5 mm is recovered. This fraction is saponified with an alcoholic solution of potassium hydroxide, then acidified and recrystallized from toluene. 2-Ethyl 5-thiazolecarboxylic acid is obtained in the form of colorless crystals, soluble in ethanol and sodium hydroxide, insoluble in water, melting at 157° C.

Analysis: $C_6H_7NO_2S$ = 157.19: Calculated: C% 45.84: H% 4.49: N% 8.91: S% 20.40: Found: C% 46.1: H% 4.5: N% 8.7: S% 20.0.

Infrared Spectrum — KBr: Bands at 3,115, 2,450, 1,850, 1,700, 1,280, 1,160, 760 and 480 cm$^{-1}$ U.V. Spectrum — ethanol: Max. at 250 mμ

The ethyl 2-chloro-3-oxo-propionate is obtained according to the process described by Elina, Majidson, C.A. 45, 9531e.

EXAMPLE II

2-Propyl-5-thiazolecarboxylic acid ($R' = CH_2CH_2CH_3$ and R = H)

Operating in the same manner as in Example I, starting from thiobutyramide, 2-propyl-5-thiazolecarboxylic acid is obtained in the form of colorless crystals, soluble in sodium hydroxide and alcohol, slightly soluble in ether, insoluble in water, melting at 137° C.

Analysis: $C_7H_9NO_2S$ = 171.22: Calculated: C% 49.10: H% 5.30: N% 8.18: S% 18.73: Found: C% 49.0: H% 5.1: N% 8.0: S% 18.6.

I.R. Spectrum — KBr: Bands at 3,115, 2,480, 1,850, 1,700, 1,280, 1,150, 745 and 480 $cm^{-1}$ U.V. Spectrum — Ethanol: Max at 253 m$\mu$ So far as one knows, this compound is not described in the literature.

EXAMPLE III

Diisopropylamine 2-propyl-5-thiazolecarboxylate

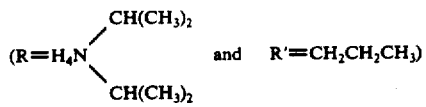

$(R=H_4N\begin{subarray}{c}CH(CH_3)_2\\CH(CH_3)_2\end{subarray}$ and $R'=CH_2CH_2CH_3)$ 4.45 Grams of 2-propyl-5-thiazolecarboxylic acid (obtained in Example II) are dissolved in 120 cc of acetone and 2.62 gm of diisopropylamine are added. The solvent is evaporated off under low pressure and the crystals thus obtained are recrystallized from isopropyl ether. The diisopropylammonium 2-propyl-5-thiazolecarboxylate is obtained in the form of colorless crystals, soluble in water and in alcohol, melting at 120° C (Yield: 90%).

Analysis: $C_{13}H_{24}N_2O_2S$ = 272.41: Calculated: N% 10.28: S% 11.77: Found: N% 10.26: S% 11.79 – 11.75.

So far as one knows this compound is not described in the literature.

EXAMPLE IV 2-n-pentyl-5-thiazolecarboxylic acid $(R' = C_5H_{11}$ and $R = H)$ Operating in the same manner as in Example I, starting from thiohexanoamide, 2-n-pentyl-5-thiazolecarboxylic acid is obtained in he form of colorless crystals, soluble in sodium hydroxide and alcohol, slightly soluble in ether, insoluble in water, melting at 90° C (Yield: 45%).

Analysis: $C_{11}H_{17}NO_2S$ = 227.33: Calculated: N% 7.03: S% 16.10: Found: N% 6.99 – 7.04: S% 16.19 – 16.15.

I.R. spectrum — KBr: Bands at 3,180, 2,480, 1,850, 1,690, 1,270, 1,150, 800 and 765 $cm^{-1}$ U.V. Spectrum — Ethanol: Max at 254 m$\mu$ So far as one knows this compound is not described in the literature.

EXAMPLE V 2-n-hexyl-5-thiazolecarboxylic acid $(R' = C_6H_{13}$ and $R = H)$

Operating in the same manner as in Example I, starting from thioheptanoamide, 2-n-hexyl-5-thiazolecarboxylic acid is obtained in the form of colorless crystals, soluble in sodium hydroxide and alcohol, insoluble in water, melting at 73° C (Yield: 39%).

Analysis: $C_{12}H_{19}NO_2S$ = 241.34: Calculated: N% 6.56: S% 15.03; Found: N% 6.35: S% 14.99.

I.R. Spectrum — KBr: Bands at 3,110, 2,480, 1,850, 1,680, 1,240, 1,150 and 755 $cm^{-1}$ U.V. Spectrum — Ethanol: Max. at 253 m$\mu$ So far as one knows this compound is not described in the literature.

EXAMPLE VI 2-n-butyl-5-thiazolecarboxylic acid $(R' = CH_2CH_2CH_2CH_3$ and $R = H)$ Operating in the same manner as in Example I, starting from thiovaleramide, 2-n-butyl-5-thiazolecarboxylic acid is obtained in the form of colorless crystals, soluble in alcohol, chloroform and benzene, insoluble in water, melting at 97° C (Yield: 55%).

Analysis: $C_8H_{11}NO_2S$ = 185.24 Calculated: N% 7.56: S% 17.31; Found: N% 7.52 – 7.47: S% 17.21 – 17.20.

I.R. Spectrum — KBr: Bands at 3,100, 2,500, 1,680, 1,270, 1,150 and 745 $cm^{-1}$ U.V. Spectrum — Ethanol: Max. at 253 m$\mu$ So far as one knows, this compound is not described in the literature.

EXAMPLE VII 2-n-undecyl-5-thiazolecarboxylic acid $(R' = (CH_2)_{10}CH_3$ and $R = H)$ Operating in the same manner as in Example I, starting from thiolauramide, 2-n-undecyl-5-thiazolecarboxylic acid is obtained in the form of colorless crystals, soluble in alcohol and acetone, insoluble in water, melting at 93° C (Yield: 31%).

Analysis: $C_{15}H_{25}NO_2S$ = 283.42. Calculated: N% 4.94: S% 11.31; Found: N% 4.92: S% 11.28.

I.R. spectrum — KBr: Bands at 2,920, 2,500, 1,700, 1,250, 1,100 and 750 $cm^{-1}$ U.V. Spectrum — Ethanol: Max. at 245 m$\mu$ So far as one knows this compound is not described in the literature.

The starting aliphatic thioamides are obtained by a process analogous to that described by Gilbert and Rumanowski, C.A., 65, 20020e.

EXAMPLE VIII

Ethyl 2-propyl-5-thiazolecarboxylate $(R' = CH_2CH_2CH_3$ and $R = CH_2CH_3)$

30 Grams of 2-propyl-5-thiazolecarboxylic acid (obtained in Example II) is dissolved in 400 cc of ethanol. A stream of hydrochloric acid gas is passed through the solution for a period of four hours while maintaining the temperature in the vicinity of 25° to 30° C. The solution is then maintained overnight. Thereafter, the mixture is evaporated to dryness. The oily residue is taken up in 10% aqueous potassium carbonate solution. The solution is extracted with ether. The organic phase is separated and washed with water until the wash waters are neutral. The organic phase is then dried, decolorized with carbon black, filtered and evaporated to dryness under vacuum. 33.1 Grams of ethyl 2-propyl-5-thiazolecarboxylate are recovered in the form of a yellow oil, being a yield of 95%.

The ester is purified by fractional distillation. 31.2 Grams of a pure product distilling at 139°–140° C under 16 mm of Hg were recovered.

The ethyl-2-propyl-5-thiazolecarboxylate occurs in the form of a liquid having an index of refraction $[N]_D^{22.5}$ = 1.5025 (Yield: 89.5%).

Analysis: $C_9H_{13}NSO_2$ = 199.26: Calculated: C% 54.24: H% 6.57: N% 7.02: S% 16.09; Found: C% 54.2: H% 6.6: N% 7.3: S% 16.0.

In TLC the product is homogeneous.

So far as one knows, this product is not described in the literature.

EXAMPLE IX

N,N-diethylamino-ethyl 2-propyl-5-thiazolecarboxylate and its chlorohydrate

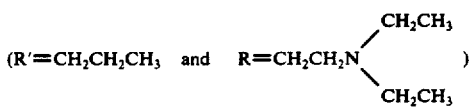

7.01 Grams of 2-propyl-5-thiazolecarboxylic acid (obtained in Example II) is placed in suspension in 150 cc of anhydrous acetone. 3.96 Grams of potassium carbonate is added thereto, then rapidly, under agitation, 8.27 gm of diethylaminoethyl chloride is added. The reaction mixture is then refluxed for a period of 10 hours.

The mixture is then cooled to room temperature; the mineral salts are removed by filtration; then the acetone is distilled off under vacuum. 12.9 Grams of the raw diethylaminoethyl ester are thus recovered. The raw ester is taken up in 100 cc of ether and 10 cc of water. The organic solution is washed with a 10% aqueous potassium carbonate solution. The organic phase is separated and washed with water. The combined aqueous phases are washed again with ether. The combined ethereal phases are washed with water and dried over magnesium sulfate.

The ether is distilled of and 11.45 gm of the crude N,N-diethylaminoethyl 2-propyl-5-carboxylate is recovered in the form of a liquid. By distillation, 9 gm of a fraction distilling at 116° to 120° C under 0.1 mm of Hg is obtained. A mew distillation furnishes 8 gm of N,N-diethylaminoethyl 2-propyl-5-thiazolecarboxylate distilling at 118°-119° C under 0.1 mm of Hg.

PREPARATION OF THE CHLOROHYDRATE 7.8 gm of the diethylaminoethyl ester are placed in 30 cc of ether and the stoichiometric amount of 2N hydrochloric acid in ethanol is added. After evaporation of the solvents, 8.8 gm of the chlorohydrate of N,N-diethylaminoethyl 2-propyl-5-carboxylate is obtained in the form of colorless crystals melting at 121°-122° C.

For analysis, the chlorohydrate is recrystallized from ethyl acetate. The melting point remained unchanged.

U.V. Spectra — Ethanol: Max. 260 mμ

Analysis: $C_{13}H_{23}N_2O_2SCl$ = 306.86: Calculated: C% 50.88: H% 7.55: Cl% 11.55: N% 9.13: S% 10.45; Found: C% 51.0: H% 7.4: Cl% 11.4: N% 9.2: S% 10.2.

The chlorohydrate of N,N-diethylaminoethyl 2-propyl-5-thiazolecarboxylate occurs in the form of colorless crystals, soluble in water, ethanol, propylene glycol, acetone, and chloroform, slightly soluble in ethyl acetate and benzene, and insoluble in ether.

So far as one knows, these products are not described in the literature.

EXAMPLE X 2,3-Isopropylidenedioxy-propyl 2-propyl-5-thiazolecarboxylate

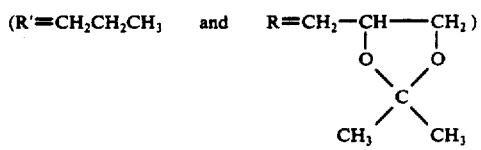

10 Grams of ethyl 2-propyl-5-thiazolecarboxylate (obtained in Example VIII) are dissolved in 66 gm of 2,3-isopropylidenedioxy-propanol. 0.57 Grams of a 50% suspenion of sodium hydride in vaseline oil is added thereto. The solution obtained is heated to 65°-70° C for 2 hours while separating the ethanol evolved. Next, 2,3-isopropylidenedioxypropanol in excess is evaporated under vacuum. The amorphous residue is taken up in 700 cc of ether and 100 cc of water.

The ethereal phase is washed with water, separated, dried, passed through carbon black, filtered and evaporated. 13 Grams of an oil is obtained, being a yield of 19%. The exter is purified by fractional distillation. The 2,3-isopropylidenedioxy-propyl 2-propyl-5-thiazolecarboxylate distills at 140° C under 0.1 mm of Hg. 10.7 Grams of pure ester is thus recovered (Yield: 75%).

Analysis: $C_{13}H_{19}NSO_4$ = 285.35: Calculated: C% 54.71: H% 6.7: S% 11.23: N% 4.90; Found: C% 55.0: H% 6.9: S% 11.4: N% 5.2.

I.R. Spectra: Conjugated CO at 1721 $cm^{-1}$. Presence of a gem-dimethyl. Absorption in the C—O—C region. c=N and c=C band at 1522 $cm^{-1}$.

Index of refraction $N_D^{23}$ = 1.4996

The 2,3-isopropylidenedioxy-propyl 2-propyl-5-thiazolecarboxylate occurs in the form of a liquid, soluble in ether, benzene and ethanol and insoluble in water.

So far as one knows, this product is not described in the literature.

EXAMPLE XI

Phenylethyl 2-propyl-5-thiazolecarboxylate

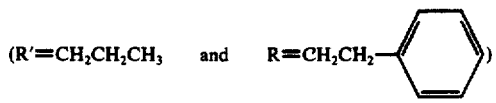

6.84 Grams of 2-propyl-5-thiazolecarboxylic acid (described in Example II) are placed in suspension in 45 cc of anhydrous ether. Over 3 minutes, 6.07 gm of triethylamine in solution in 15 cc of acetone are added thereto. A limpid solution is obtained. The solution is poured than into a solution of 5.42 gm of ethyl chloroformiate in 25 cc of anhydrous acetone while maintaining the temperature of the reaction medium between 6° and 8° C over a period of 15 minutes. The mixture is then agitated for one hour at ambiant temperature and then filtered. 4.88 Grams of phenylethanol in 45 cc of acetone are added over 5 minutes. The mixture is then agitated for 40 hours; then the solvents are distilled off. 13 Grams of raw phenylethyl 2-propyl-5-thiazolecarboxylate is thus obtained.

The raw product is dissolved in 140 cc of ether and the ethereal solution is washed twice with 15 cc of a 5% aqueous potassium carbonate solution, then with water.

The ethereal phase is next dried, treated with carbon black, filtered and evaporated to dryness. 9.52 Grams of a clear yellow oil are thus recovered.

The phenylethyl 2-propyl-5-thiazolecarboxylate is next rectified by fractional distillation under vacuum. 4.72 Grams of pure ester are recovered between 140° to 150° C under 0.1 mm of Hg in the form of a clear yellow liquid product, soluble in ether and acetone and insoluble in water.

Analysis: $C_{15}H_{17}NO_2S$ = 275.36: Calculated: C% 65.42: H% 6.22: N% 5.09: S% 11.64; Found: C% 65.5: H% 6.4: N% 4.9: S% 11.5.

U.V. Spectra — Ethanol: Max 252 M$\mu$ $E_{1\,cm}^{1\%}$ = 420 Index of refraction $N_D^{23°}$ = 1.5495.

So far as one knows, this product is not described in the literature.

EXAMPLE XII

α-glyceryl 2-propyl-5-thiazolecarboxylate (R' = $CH_2CH_2CH_3$ and R = $CH_2CHOHCH_2OH$)

The 2,3-isopropylidenedioxy-propyl 2-propyl-5-thiazolecarboxylate of Example X is subjected to acidic hydrolysis to remove the acetonide and α-glyceryl 2-propyl-5-thiazolecarboxylate is recovered, having a melting point of 71° C (isopropylether) in a yield of 62%.

EXAMPLE XIII

Methyl 2-propyl-5-thiazolecarboxylate

R' = $CH_2CH_2CH_3$ and R = $CH_3$)

Following the esterification process of Example VIII, but utilizing methanol, methyl 2-propyl-5-thiazolecarboxylate is recovered having a boiling point of 129° C under 14 mm of Hg with a yield of 88%.

EXAMPLE XIV

Morpholinylethyl 2-propyl-5-thiazolecarboxylate and its chlorohydrate (R'=$CH_2CH_2CH_3$ and R=$CH_2CH_2N\underset{\underset{}{\diagdown}}{\diagup}\!\!\!\!\!\!\bigcirc\!\!\!\!\!\!\underset{\underset{}{\diagup}}{\diagdown}O$)

Following the transesterification process of Example X, but utilizing morpholinylethanol, morpholinylethyl 2-propyl-5-thiazolecarboxylate is recovered and, following the procedure of Example IX, preparation of the chlorohydrate, the chlorohydrate of morpholinylethyl 2-propyl-5thiazolecarboxylate is recovered after recrystallization from isopropanol in the form of crystals melting at 180° c with a yield of 63%.

EXAMPLE XV

Tert.-butyl 2-propyl-5-thiazolecarboxylate (R'=$CH_2CH_2CH_3$ and R=$C(CH_3)_3$)

Following the esterification process of Example VIII, but utilizing tert.-butanol, tert.-butyl 2-propyl-5-thiazolecarboxylate is recovered having a melting point of 48° C (hexane) with a yield of 48%.

EXAMPLE XVI

Pyridylmethyl 2-propyl-5-thiazolecarboxylate

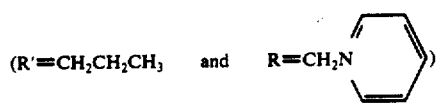

Following the transesterification process of Example X, but utilizing pyridylmethanol, pyridylmethyl 2-propyl-5-thiazolecarboxylate is recovered.

EXAMPLE XVII

Benzyl 2-propyl-5-thiazolecarboxylate

R' = $CH_2CH_2CH_3$ and R = $CH_2O_6H_5$)

8.5 grams 2-propyl-5thiazolecarboxylic acid are dissolved under atmosphere of nitrogen into a mixture of 5.4 grams of benzyl alcohol and 75 cc of tetrahydrofuran. After cooling to 0° C a solution of 10.3 grams of dicyclohexyl carbodiimide in 75 cc of tetrahydrofuran is added. Then the mixture is warmed to room temperature and left during 22 hours.

The precipitate is filtered and the filtrate evaporated to dryness. The oily residue is extracted twice with ether. The organic solution is washed with a 10 percent sodium carbonate solution then with water until the pH of the aqueous washings reaches a pH of 6.

The organic solution is dried on sodium sulfate, filtered, decolorized with charcoal, filtered and evaporated under reduced pressure.

The raw ester is then purified by chromatography on silica gel and elution with a mixture of ethyl acetate and cyclohexane; 4 grams of benzyl 2-propyl-5-thiazolecarboxylate are thus recovered.

The benzyl 2-propyl-5-thiazolecarboxylate is a yellow oil soluble in ether and ethanol, insoluble in water. Its refraction index $N_D^{20}$ = 1.5547.

Analysis: $C_{14}H_{15}NSO_2$ = 26.33: Calculated C% 64.33: H% 5.78: N% 5.36: S% 12.26; Found C% 64.3: H% 5.5: N% 5.5: S% 12.0.

The various salts and esters of other 2-alkyl-5-thiazolecarboxylic acids can be produced following the processes of Examples III and VIII to XVI, using the acids of Examples I and IV to VII.

PHARMACOLOGICAL DATA

1. Determination of the acute toxicity:

The acute toxicity has been determined on batches of ten mice weighing from 18 to 22 gm. The products were administered in suspension in gum arabic solution in water, at increasing doses, either by oral route or by intraperitoneal route.

The animals are kept under observation for one week. The average lethal dose (LD$_{50}$) is determined graphically by the method of Dragstedt and Lang.

TABLE I

| Products | Intraperitoneal Route | Oral Route |
|---|---|---|
| 2-methyl-5-thiazole-carboxylic acid | | >2 gm/kg |
| 2-ethyl-5-thiazole-carboxylic acid | 525 mg/kg | >2 gm/kg |

TABLE I-continued

| Products | Intraperitoneal Route | Oral Route |
|---|---|---|
| 2-propyl-5-thiazole-carboxylic acid | 1,680 mg/kg | >2 gm/kg |

2. Determination of hypolipemiant activity:

The hypolipemiant activity has been determined on the rat according to the technique of Jacobs et al, Proc. Soc. Exp. Biol. Med., [1965], 119 (4) pp.1117–1120.

Male rats of the Wistar strain weighing from 160 to 180 gm are not fed for 24 hours. The products employed in a 5% suspension in gum arabic solution in water, are administered through an oesophagial probe at doses of 20, 40 and 80 mg/kg. Four hours after ingestion of the product, some blood is withdrawn on which a determination of the triglycerides is carried out.

The principle of the determination is as follows:

The serum lipids are extracted with petroleum ether in the presence of ethanol. The lipidic solution is treated several times with 87% ethanol. A solution is thus obtained, the upper part of which contains the glycerides and the lower part, the phospholipids.

The weight of the glycerides is determined by determination of glycerol by periodic acid oxidation and determination of the formaldehyde with chromotropic acid.

The results obtained are summarized in the following Table II.

TABLE II

| Products | Doses | Percentage of Reduction by Comparison With Controls |
|---|---|---|
| 2-methyl-5-thiazole-carboxylic acid | 20 mg/kg | 40 |
| 2-ethyl-5-thiazole-carboxylic acid | 20 mg/kg | 50 |
| 2-propyl-5-thiazole-carboxylic acid | 20 mg/kg | >50 |

These results demonstrate that the activity of the products studied upon the blood lipids is very clear.

3. Peripheral vasodilatory effect:

The peripheral vasodilatory effect has been investigated on the guinea pigs with non-pigmented ears by the appearance of the reddening of the ear.

The animals, after being starved, are administered the products by oral route, at different dosages. The time of appearance of a reddening of the ears, the duration of this reddening and its intensity, which is recorded subjectively from 0 to +++ is determined.

The following Table III summarizes the results obtained.

TABLE III

| Products | Doses mg/kg | Period of Induction min. | Duration min. | Intensity |
|---|---|---|---|---|
| 2-methyl-5-thiazole-carboxylic acid | 10 | 5 | 30 | +++ |
| | 20 | 3 | 32 | +++ |
| | 50 | 3 | 35 | +++ |
| 2-ethyl-5-thiazole-carboxylic acid | 50 | 6–8 | 50 | +++ |
| | 100 | 6–7 | 60 | +++ |
| 2-propyl-5-thiazole-carboxylic acid | 50 | 13 | 30 | + |
| | 100 | 10 | 32 | ++ |

These results show that the products studied possess a marked peripheral vasodilatory activity.

COMPARISON TESTS

The following tests with ethyl 2-n-propylthiazole-4-carboxylate (described by Geiger et al, C.A., 67, 11413) were conducted.

TEST DATA

A. Determination of hypolipemiant activity:

The hypolipemiant activity was determined on the rat using the technique of Jacobs et al (Proc. Soc. Exp. Biol. Med., [1965], 119 [4], pp. 1117–1120). Male rats of the Wistar strain weighing from 160 to 180 gm were not fed for 24 hours. The product employed in a 5% suspension in gum arabic solution in water, was administered orally through an oesophagial probe at doses of 20 and 80 mg/kg. Four hours after ingestion of the product, some blood was withdrawn and a determination of the triglycerides therein was made.

The principle of the determination is as follows:

The serum lipids are extracted with petroleum ether in the presence of ethanol and the lipidic solution was treated several times with 87% ethanol to obtain a solution, the upper part of which contained the glycerides and the lower part the phospholipids. The weight of the glycerides by determination of glycerol by periodic acid oxidation and determination of the formaldehyde with chromotropic acid is estimated. There was no action on the triglycerides by ethyl 2-n-propyl-thiazole-4-carboxylate at either dose.

B. Peripheral vasodilatory effect:

The peripheral vasodilatory effect was investigated on guinea pigs with non-pigmented ears by the appearance of the reddening of the ear. The animals were starved and the product was administered intraperitoneally at a dose of 100 mg/kg. The time of appearance of a reddening of the ears, the duration of this reddening and its intensity being recorded subjectively from 0 to +++ is determined.

The test showed no vasodilatory activity for the said ester, ethyl 2-n-propyl-thiazole-4-carboxylate, at this dosage.

C. Hypothermic activity:

The hypothermic activity was determined on guinea pigs by administering the test compound, ethyl 2-n-propyl-thiazole-4-carboxylate, intraperitoneally at a dose of 100 mg/kg. The body temperature of the guinea pigs was determined ½ hour before the administration of the test compound and then 1, 2 and 3 hours after the said administration. There was no hypothermic activity at the dose of 100 mg/kg.

D. Determination of the acute toxicity:

The acute toxicity was determined on batches of ten mice weighing from 18 to 22 gm. Ethyl 2-n-propyl-thiazole-4-carboxylate was administered in suspension in gum arabic solution in water, at increasing doses by the intraperitoneal route. The animals were kept under observation for one week. The average lethal dose ($LD_{50}$) was determined graphically by the method of Dragstedt and Lang. The $DL_{50}$ in this test fell between 1000 and 1500 mg/kg.

It can be concluded from the above comparison test that ethyl 2-n-propyl-thiazole-4-carboxylate has no hypothermic or vasodilatory activity at an intraperitoneal dose of 100 mg/kg and no hypolipemiant activity at an oral administration of 20 and 80 mg/kg, compared with the products of the invention as reported in Tables I, II and III.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A hypolipemiant composition comprising an effective amount of at least one 2-alkyl-5-thiazolecarboxylic acid derivative of the formula

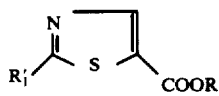

wherein R is a member selected from the group consisting of hydrogen, an alkali-metal, triethylammonium, diisopropylammonium, diethylammonium, ethanolammonium, collidinium, morpholinium, piperidinium, alkyl having 1 to 10 carbon atoms, benzyl, the alkyl residue of an alkylheterocyclic alcohol the alkyl residue of which contains 1 to 6 carbon atoms and of which the heterocyclic residue is selected from the group consisting of furyl, thienyl and pyridyl, α-glyceryl, diethylaminoethyl, diethylaminopropyl and dipropylaminoethyl, and $R'_1$ is a linear alkyl or 1 to 12 carbon atoms, and a major amount of a pharmaceutical carrier.

2. A hypolipemiant composition comprising an effective amount of at least one 2-alkyl-5-thiazolecarboxylic acid derivative of the formula

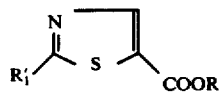

wherein R is a member selected from the group consisting of hydrogen, an alkali metal, triethylammonium, diisopropylammonium, diethylammonium, ethanolammonium, collidinium, morpholinium, piperidinium, and alkyl having 1 to 10 carbon atoms and $R'_1$ is a linear alkyl of 1 to 12 carbon atoms, and a major amount of a pharmaceutical carrier.

3. The hypolipemiant composition of claim 2 wherein R is hydrogen and R' is n-propyl.

4. The hypolipemiant composition of claim 2 wherein R' is n-propyl.

5. The hypolipemiant composition of claim 2 wherein R is hydrogen.

6. A method of reducing the amount of sanguine lipids in warm-blooded animals which comprises administering to said warm-blooded animals a safe and effective amount of at least one 2-alkyl-5-thiazolecarboxylic acid derivative of the formula

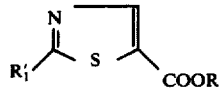

wherein R is a member selected from the group consisting of hydrogen, an alkali-metal, triethylammonium, diisopropylammonium, diethylammonium, ethanolammonium, collidinium, morpholinium, piperidinium, alkyl having 1 to 10 carbon atoms, benzyl, the alkyl residue of an alkylheterocyclic alcohol the alkyl residue of which contains 1 to 6 carbon atoms and of which the heterocyclic residue is selected from the group consisting of furyl, thienyl and pyridyl, α-glyceryl, β-glyceryl, diethylaminoethyl, diethylaminopropyl and dipropylaminoethyl, and $R'_1$ is a linear alkyl of 1 to 12 carbon atoms.

7. A method of reducing the amount of sanguine lipids in warm-blooded animals which comprises administering to said warm-blooded animals a safe and effective amount of at least one 2-alkyl-5-thiazolecarboxylic acid derivative of the formula

wherein R is a member selected from the group consisting of hydrogen, an alkali metal, triethylammonium, diisopropylammonium, diethylammonium, ethanolammonium, collidinium, morpholinium, piperidinium, and alkyl having 1 to 10 carbon atoms and $R'_1$ is a linear alkyl of 1 to 12 carbon atoms.

8. The method of claim 7 wherein R is hydrogen and $R'_1$ is n-propyl.

9. The method of claim 7 wherein $R'_1$ is n-propyl.

10. The method of claim 7 wherein R is hydrogen.

11. The method of claim 7 wherein R is hydrogen and $R'_1$ is methyl.

12. The method of claim 7 wherein R is hydrogen and $R'_1$ is ethyl.